US010632281B2

(12) United States Patent
Rosenman et al.

(10) Patent No.: US 10,632,281 B2
(45) Date of Patent: Apr. 28, 2020

(54) DRUG DELIVERY CATHETERS THAT ATTACH TO TISSUE AND METHODS FOR THEIR USE

(71) Applicant: BioCardia, Inc., San Carlos, CA (US)

(72) Inventors: Daniel C. Rosenman, San Carlos, CA (US); Peter A. Altman, San Carlos, CA (US); Brian K. Hakim, San Carlos, CA (US); Daniel J. Kayser, San Carlos, CA (US); Robert E. Maston, San Carlos, CA (US); Douglas McEtchin, San Carlos, CA (US)

(73) Assignee: BioCardia, Inc., San Carlos, CA (US)

( * ) Notice: Subject to any disclaimer, the term of this patent is extended or adjusted under 35 U.S.C. 154(b) by 1022 days.

(21) Appl. No.: 14/257,895

(22) Filed: Apr. 21, 2014

(65) Prior Publication Data

US 2014/0228748 A1    Aug. 14, 2014

Related U.S. Application Data

(63) Continuation of application No. 12/200,812, filed on Aug. 28, 2008, now abandoned, which is a
(Continued)

(51) Int. Cl.
*A61M 25/00* (2006.01)
*A61M 25/01* (2006.01)
*A61M 25/04* (2006.01)

(52) U.S. Cl.
CPC .... *A61M 25/0084* (2013.01); *A61M 25/0014* (2013.01); *A61M 25/0068* (2013.01);
(Continued)

(58) Field of Classification Search
CPC .......... A61M 25/0084; A61M 25/0014; A61M 25/0136; A61M 25/0068; A61M 25/0147; A61M 2025/0175; A61M 25/0097
See application file for complete search history.

(56) References Cited

U.S. PATENT DOCUMENTS

| 5,030,204 A | * | 7/1991 | Badger | ............. A61M 25/0152 600/434 |
| 5,843,028 A | * | 12/1998 | Weaver | .................. G01R 19/10 604/101.05 |

(Continued)

*Primary Examiner* — Bradley J Osinski
(74) *Attorney, Agent, or Firm* — K. David Crockett, Esq.; Crockett & Crockett, PC

(57) ABSTRACT

A system and method for delivering a drug to a target site within a patient's body. The system and method include a steerable guide catheter and a drug delivery catheter. The steerable guide catheter has a first extension tube and a second extension tube that are joined together and form a shoulder. The delivery catheter has a distal docking segment and a proximal docking segment. The guide catheter is inserted into the patient's body, then the delivery catheter is inserted into the guide catheter. The distal docking segment engages the first extension tube, the proximal docking segment engages the second extension tube, and the shoulder limits the distance the delivery catheter can be inserted into the guide catheter. Also, once the delivery catheter is inserted it can be rotated to attach the helical tip to the target site. The guide catheter also includes a steering mechanism as well as a friction mechanism which controls the tension on the steering mechanism. The delivery catheter also includes two luer fittings, each having its own lumen.

28 Claims, 14 Drawing Sheets

Related U.S. Application Data continuation of application No. 11/439,628, filed on May 23, 2006, now abandoned, which is a continuation of application No. 10/353,233, filed on Jan. 27, 2003, now Pat. No. 7,048,711, which is a continuation of application No. 09/746,986, filed on Dec. 22, 2000, now Pat. No. 6,511,471.

(52) U.S. Cl.
CPC .... *A61M 25/0136* (2013.01); *A61M 25/0138* (2013.01); *A61M 25/0147* (2013.01); *A61M 25/0045* (2013.01); *A61M 25/0069* (2013.01); *A61M 25/0097* (2013.01); *A61M 25/04* (2013.01); *A61M 2025/0081* (2013.01); *A61M 2025/0089* (2013.01); *A61M 2025/0175* (2013.01); *A61M 2202/0468* (2013.01)

(56) References Cited

U.S. PATENT DOCUMENTS

| | | | | |
|---|---|---|---|---|
| 5,911,715 A | * | 6/1999 | Berg | A61M 25/0009 138/125 |
| 2001/0007933 A1 | * | 7/2001 | Lesh | A61B 17/22 604/272 |

* cited by examiner

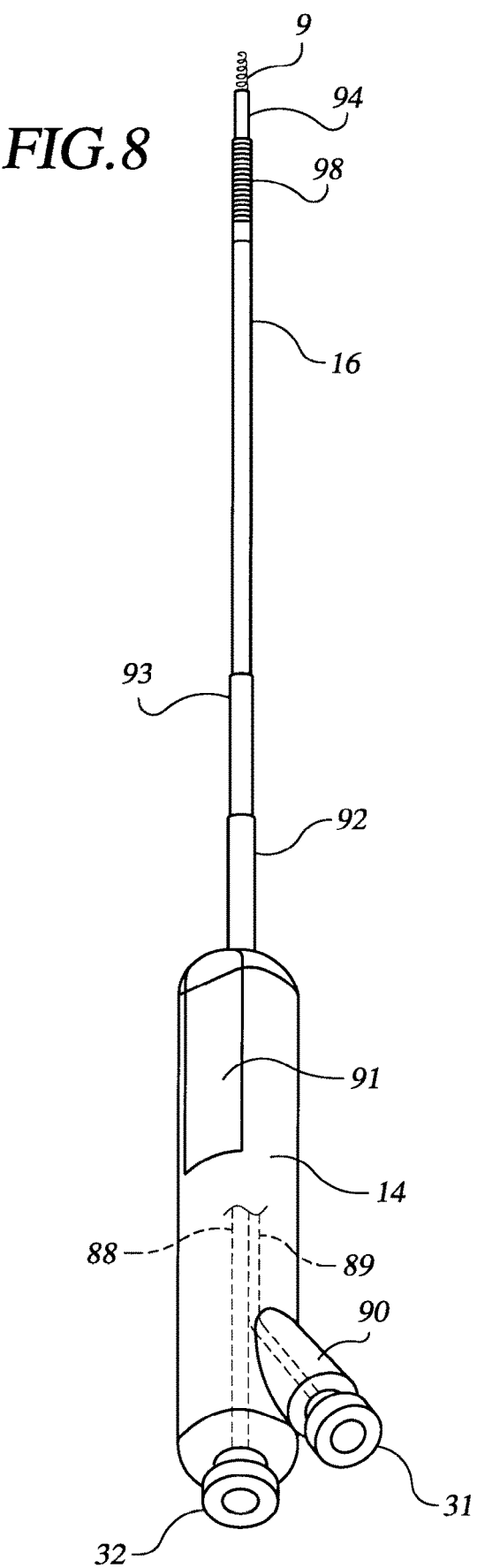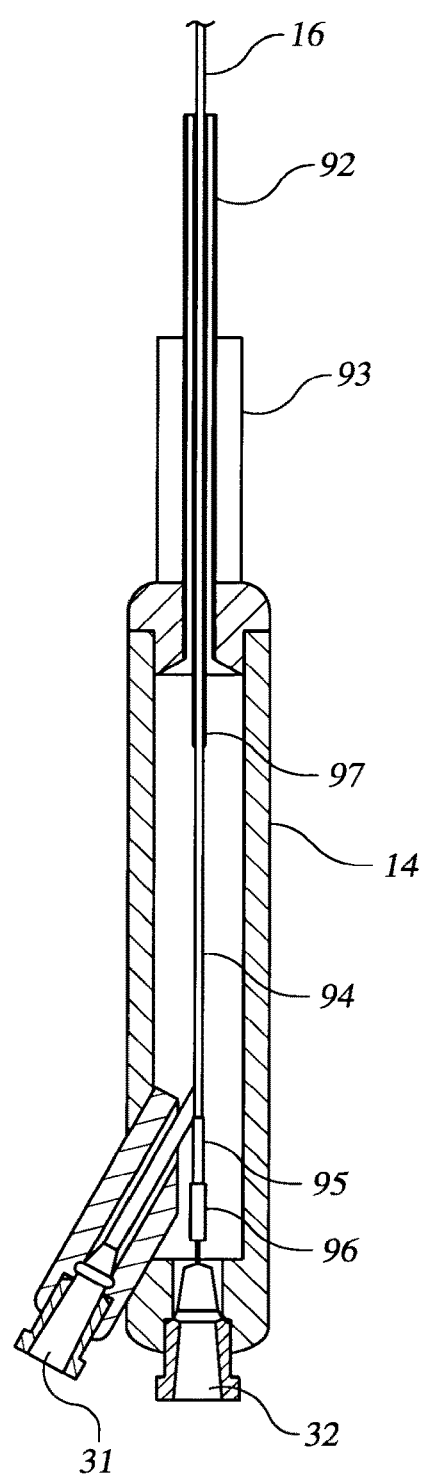

DRUG DELIVERY CATHETERS THAT ATTACH TO TISSUE AND METHODS FOR THEIR USE

This application is a continuation of U.S. application Ser. No. 12/200,812, filed Aug. 28, 2008, which is a continuation of U.S. patent application Ser. No. 11/439,628, filed May 23, 2006, which is a continuation of U.S. application Ser. No. 10/353,233, filed Jan. 27, 2003, now U.S. Pat. No. 7,048,711, which is a continuation of U.S. application Ser. No. 09/746,986 filed Dec. 22, 2000, now U.S. Pat. No. 6,511,471.

FIELD OF THE INVENTIONS

The inventions described below relate to site-specific delivery of therapeutic agents, structures and catheter systems to achieve site-specific delivery of therapeutic agents, and means for implanting and using these systems to enable delivery of therapeutic agents to the body.

BACKGROUND OF THE INVENTIONS

We have been developing catheter systems which enable injection of therapeutic agents into the heart in very precise doses and locations within the heart. The catheter systems use a helical needle, mounted on the distal end of a catheter, to secure the device to the heart wall prior to and during injection. With the helical needle, the injection site can be chosen, mechanically engaged, viewed and confirmed, and maintained for relatively long intraoperative periods or chronically. The helix prevents dislodgment of the needle during injection or during an extended period of injections. Rudimentary mechanisms have been proposed for insertion and rotation of the helix, which must be accomplished from the proximal end of the catheter system. The devices described below provide mechanisms for inserting and driving the drug delivery catheter into the heart, as well as connecting the requisite drug reservoirs to the catheter.

SUMMARY

Several embodiments of catheter systems designed to facilitate drug delivery into the heart are described below. The catheter systems include a steerable guide catheter and a drug delivery catheter designed for use together. The drug delivery catheter is inserted through the lumen of the guide catheter, and its handle is dockable within the handle of the guide catheter. Integrated design of the drug delivery catheter with the steerable guide catheter provides for a keyed or matched assembly of the device which provides for limited or controlled extension of the drug delivery catheter tip from the guide catheter tip. In one embodiment, the drug delivery and steerable guide mechanisms are integrated in a single piece handle, and distensible tubing on the proximal end of the drug delivery catheter allows rotation of the drug delivery catheter tube relative to the guide catheter tube and Luer fitting which are in fluid communication with the drug delivery catheter.

BRIEF DESCRIPTION OF THE DRAWINGS

FIG. 8 is an isometric view of another delivery catheter.

FIG. 9 is the cross section view of the handle of the delivery catheter in FIG. 8.

DETAILED DESCRIPTION OF THE INVENTIONS

New concepts for delivering agents for the treatment of heart failure, ischemia, arrhythmias, and restenosis are disclosed. The main embodiment consists of transvenous or transarterial catheter delivery techniques for delivering agents directly to a chosen site within the heart at a depth within the heart tissue. Hollow helical delivery devices, needle delivery devices, and implantable controlled release matrices may be inserted such that metabolic agents, anti-ischemic agents, growth factors, antiarrhythmic agents, anti-inflammatory agents, gene therapy preparations, cells, cellular material and combinations of these agents may be delivered directly to the tissue that can benefit most from these agents. These systems have applicability in many areas of the body, particularly those that may be accessed via a body duct or vessel.

These drug delivery structures may be made from drastically different materials depending upon whether the device is to be used chronically or acutely. For example, metal components in the implantable embodiments, which are formed of a Platinum Iridium alloy consisting of ninety percent Platinum and ten percent Iridium, will typically be replaced with 316L surgical stainless steels in the acute embodiments. Likewise implantable grades of silicone and polyurethane will be replaced with polyurethanes, polyolefins, fluoropolymers, nylon, and the like in the acute uses of the devices. As a means of addressing this, the term catheter is used to describe both chronically and acutely implantable systems.

Figure 1:
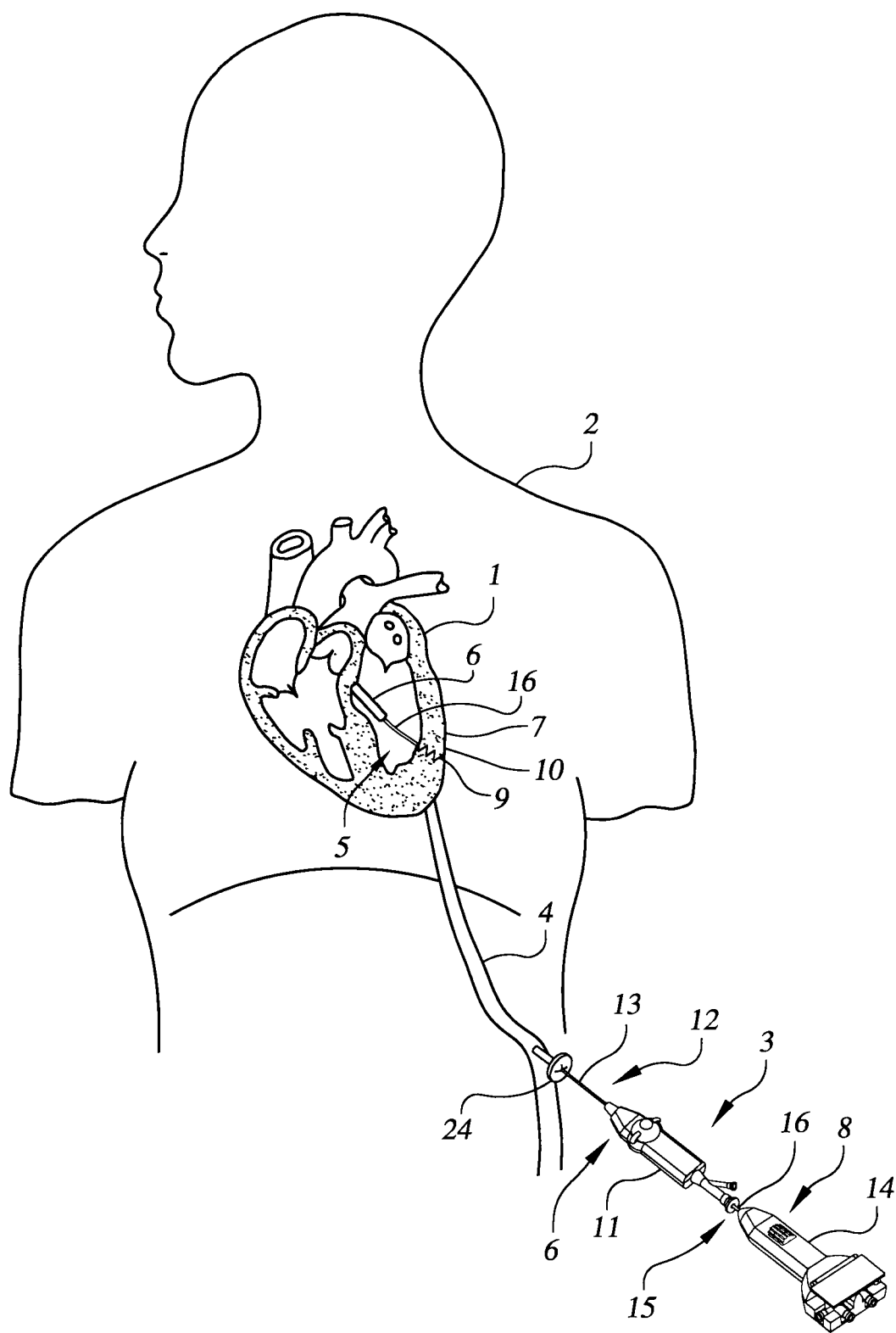
FIG. 1 shows an external view of the devices entering a patient's vasculature and routing into the heart.

FIG. 1 illustrates the use of the devices described in more detail below. FIG. 1 shows a sectional view of the heart 1 within a patient 2. A steerable drug delivery catheter system 3 is in placed within the patient, having been percutaneously inserted into an artery such as the femoral artery, and passed retrograde across the aorta 4 and into the left ventricular chamber 5 over a guide wire (not shown). Steerable guide catheter 6 is advanced through the patient's vasculature into the left ventricle in order to target a region of the heart wall 7 for delivery. A drug delivery catheter 8 with a fixation element 9 has been inserted through the guide catheter, so that the distal tip of the delivery catheter and the fixation element are proximate the target region of the heart. Once oriented toward a region of the heart wall 7 within, for example, the left ventricle wall 10, the delivery catheter 8 is advanced into the heart wall 10 and fixed to the heart tissue by means of the fixation element, which is a helical tip 9. Operation of the steerable guide catheter is controlled with the steerable catheter handle 11 mounted on the proximal end 12 of the steerable guide catheter tube 13. The drug delivery catheter is controlled with the drug delivery catheter handle 14 mounted on the proximal end 15 of the drug delivery catheter tube 16. The drug delivery catheter tube is inserted into the guide catheter tube through the steerable catheter handle.

Figure 2:
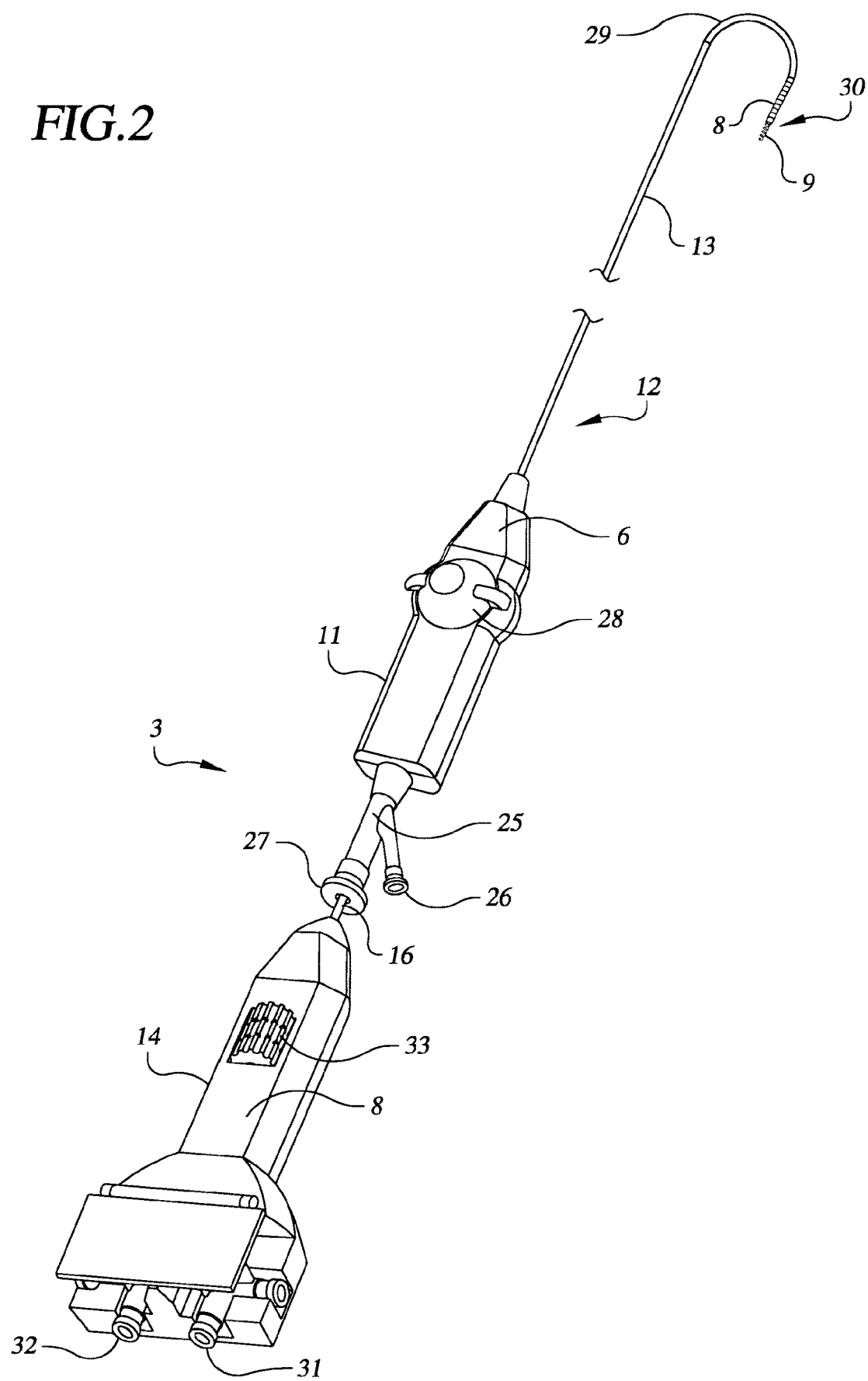
FIG. 2 shows an isometric view of the steerable guide with a delivery catheter inside it.

FIG. 2 shows steerable drug delivery catheter system 3 with the steerable guide catheter 6 and dockable delivery catheter 8 assembled in their working relationship. The steerable guide catheter 6 typically enters the patient's vasculature in the femoral artery or vein located in the patient's thigh, through an appropriately sized hemostatic sheath introducer (item 24 in FIG. 1), which prevents bleeding at the entrance to the femoral vessel. Attached to the proximal end 12 of the steerable guide catheter handle 11 is a hemostatic "Y" adapter 25 with a sidearm Luer fitting 26 and proximally aligned closable ring seal 27. The hemostatic "Y" adapter provides a seal that opens and closes an orifice when the surgeon actuates the closable ring seal. The internal diameter of the orifice can be varied from an opening of 0.125" in diameter down to a hemostatically closed condition, so that the drug delivery catheter can be inserted and removed while the guide catheter is in place in the patient's body without excessive backflow of blood. The side arm 26 of the hemostatic "Y" adapter can be used by the doctor to infuse radiopaque contrast agent or withdraw blood or other fluids through the steerable guide catheter. The steering knob 28 is mounted on the outside of the steerable guide catheter handle 11, and is rotatable to cause deflection or steering of the distal segment 29 of the steerable guide catheter. The segment of the catheter which bends in response to steering input is referred to as the steering segment, and can be adjusted in length and arc as described below.

Again referring to FIG. 2, the delivery catheter tube 16 is inserted through the seal of the hemostatic "Y" and through the steerable guide catheter 6 to its position in the heart. The distal tip 30 of the drug delivery catheter, when desired by the surgeon, may be extended distally from the distal tip of the guide catheter. The drug delivery catheter handle 14 is fitted with one or more Luer fittings 31 and 32 which communicate with lumens within the drug delivery catheter, and, as illustrated in the cross sections below, provide fluid communication with the distal tip of the drug delivery catheter and the fixation element. The thumbscrews 33 within the handle 14 are rotatable by the surgeon, and operate to rotate the drug delivery catheter tube 16, distal tip and helical tip 9.

The devices are used together to infuse therapeutic agents to tissues in the body that are accessible through ducts or vasculature. The doctor inserts the steerable guide catheter through the femoral hemostatic sheath into the femoral vessel. The guide may or may not have a guidewire inside it. The guidewires are commercially available medical devices that help route catheters to their ultimate position in the body. They are commonly stainless steel or PTFE covered stainless steel coils that are 0.065" in diameter or less and 90-180 centimeters in length. They come in varying stiffness and end shapes (straight or j-tipped). The steerable guide catheter is routed up the artery until it reaches the aortic arch. The doctor may advance and retract the guidewire during the installation as desired. The guide catheter can also be steered (curved) by the doctor by actuating the steering knob 28 during advancement. Once the distal tip of the guide gets to the aortic valve, the guidewire may be prolapsed into the ventricle. The steerable guide catheter is then advanced across the valve into the left ventricle over the guidewire and the guidewire is removed. Alternately, the steerable guide can be curved to its tight radius shape to 180 degrees of curvature or more and prolapsed across the aortic valve without the use of a guidewire. The doctor may choose to infuse radiopaque contrast agent through the guide at this time by hand or with a power injector to create a radiographic ventriculogram or x-ray picture of the shape and structures of the ventricle.

The drug delivery catheter tube 16 is now inserted into the steerable guide catheter 6 through the hemostatic adapter 25 until the tip of the delivery catheter is coincident with end of the steerable guide catheter. This position can be seen on the fluoroscopic monitors or can be indicated by marks on the proximal shaft of the delivery catheter. The steerable guide catheter 6 is now curved by actuation of the steering knob 28 and rotated by rotating the handle to position the delivery catheter tube 16 toward the tissue to be treated. (The thumbscrews 33 have been designed to limit the number of rotations that the doctor may make, to prevent over-penetration of the helical tip in the myocardium. If the doctor is not satisfied with initial placement, or wants to reposition the helical tip for additional treatment, the thumbscrews must be operated to withdraw to helical tip prior to another attempt to drive the helical tip into the heart). The delivery catheter tube 16 is then extended until the tip of the catheter touches the tissue to be treated. The surgeon rotates the thumbscrews 33 in the handle of the delivery catheter 8 and advances the helical tip 9 into the tissue to be treated. The surgeon may view the catheters under fluoroscopic or other real time imaging systems. He can infuse contrast through the side arm 26 of the hemostatic adapter around the delivery catheter tube 16 and toward the tissue of interest. He can infuse contrast agent from the end of the delivery catheter that is not embedded in the tissue through one of the stopcocks on the delivery catheter handle. The last alternative is to infuse tissue-compatible imaging agent through the lumen connected to the hollow helical needle and out of the tip of the needle itself. This last modality may allow the doctor to judge the vascularity of the tissue in the area as well as the depth of the helical tip by the rate at which the tissue takes away the contrast media. The doctor may also monitor the electrical signal obtained from a wire connected to the distal helical tip to confirm penetration of the myocardium.

Once the doctor is satisfied with the depth and location of the needle tip, the therapeutic agent is infused through the hollow helical needle. The doctor can control the volume, pressure, rate and amount of therapeutic agents delivered. Several therapeutic agents can be delivered in series. Flushing agent can be delivered before or after the therapeutic agent to change the distribution patterns. Other agents can be infused systemically preceding, concomitant, or following this treatment. Other agents can be delivered to the left ventricular free space through the second lumen in the delivery catheter or through the guide via the side arm of the hemostatic "Y". Agents can be infused by hand with syringes of various sizes and volumes or using powered pumps or injectors.

After the delivery sequence is complete, the doctor rotates the delivery thumbscrews 33 and detaches the helical tip 9 of the delivery catheter 8 from the heart wall. At this time, the tip of the delivery catheter can be retracted into the steerable guide catheter 6 by moving the handles relative to one another. The guide may then be steered to another location by changing its curve with the steering knob 28 or rotating its handle. If another infusion is desired, the process is repeated for that site. Alternatively, the delivery catheter can be fully withdrawn from the body, the guide repositioned, the delivery catheter reinserted and another infusion given.

Another use of the side arm on the hemostatic "Y" is to drip saline or heparinized saline around the delivery catheter and through the guide catheter during use. This method is thought to minimize the chance of thrombus formation on the devices during extended procedures.

Figure 3:
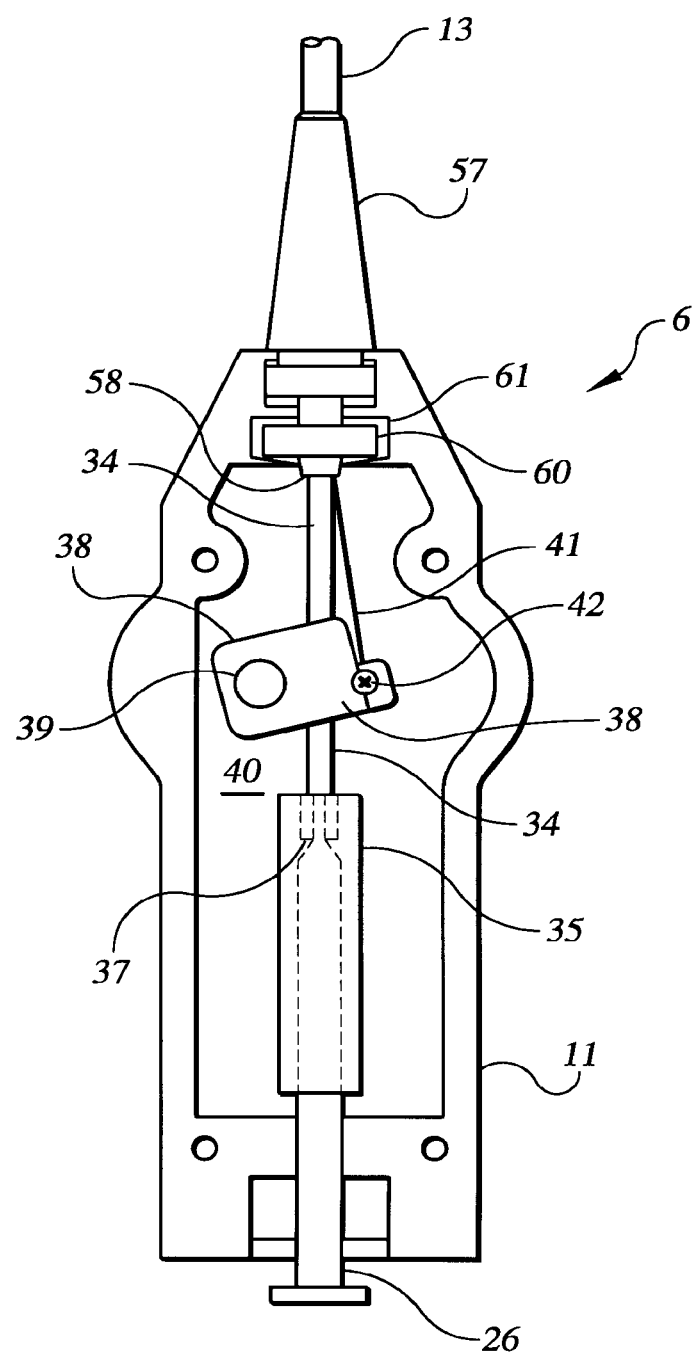
FIG. 3 shows an internal view of the guide catheter handle and its mechanisms.

FIG. 3 shows the inside of the steerable guide handle 11 with the top half of the handle and the steering knob 28 removed to reveal the inner components of the handle. The steering components rest within the bottom half of the handle. The guide catheter tube 13 is connected to the Luer fitting 26 on the proximal end of the handle through the a first extension tube 34 of the guide catheter tube, which may include a relatively large bore (second) extension tube 35 that runs through the center of the proximal half of the handle of the steerable guide catheter tube 13. The second extension tube 35 has an inner diameter of 0.125" that is slightly larger than the diameter of the docking portion of the delivery catheter that fits within it. The joint at which the proximal butt end of the first extension tube 34 meets the second extension tube presents a shoulder 37. The shoulder limits distal movement of the drug delivery catheter, which, as shown below, includes a distally facing shoulder matching the proximal shoulder of the guide catheter. The length of the large bore extension tube 35 is matched to the length of the drug delivery catheter to limit the throw of the drug delivery catheter to the desired maximum distal movement of the drug delivery catheter beyond the guide catheter.

The mechanism that allows passage of the first extension 34 through the center of the handle while providing a centrally located steering knob is the "U"-shaped rocker or crank 38 that is mounted on pin 39 fixed to one of the handle halves (in this case, fixed to the inside surface 40 of the handle bottom). The U-shaped crank 38 is pinned to the housing half via the pin which is positioned off the central axis of the housing, displaced radially toward the handle outer edge. This provides an off-center rotational axis for the crank. The steering pullwire 41 of the steerable guide catheter is secured to the crank, with the attachment point displaced radially (across the radius of the handle) so that rotation of the crank about the pin causes longitudinal motion of the pullwire. The steering pullwire 41 is clamped to the U-shaped crank 38 under a setscrew 42 that is screwed into the crank.

The pullwire 41 may have a metal or polymer sleeve crimped, glued, or slid on its end to protect it from being crushed by the setscrew. The pullwire may be solid, stranded, coated, or wound and is typically constructed of stranded Kevlar, highly oriented polymer, or metal such as stainless steel and coated with fluoropolymer. The pullwire 41 is typically between 0.002 and 0.015 inches in diameter and preferably 0.006" in diameter. The pullwire may be either round in cross section or flattened such as an oval, rectangle, or ribbon. As shown in FIG. 3, the steering knob 28 for the pullwire 41 is attached to the crank 38 through one of the housing halves, in this case the upper half. The steering knob 28 causes the crank 38 to rotate about the pin which tensions the pullwire 41 when the steering knob 28 is actuated. The steering knob 28 may be duplicated on both the bottom and top housing halves to allow the steering from either side of the catheter.

Figure 4:
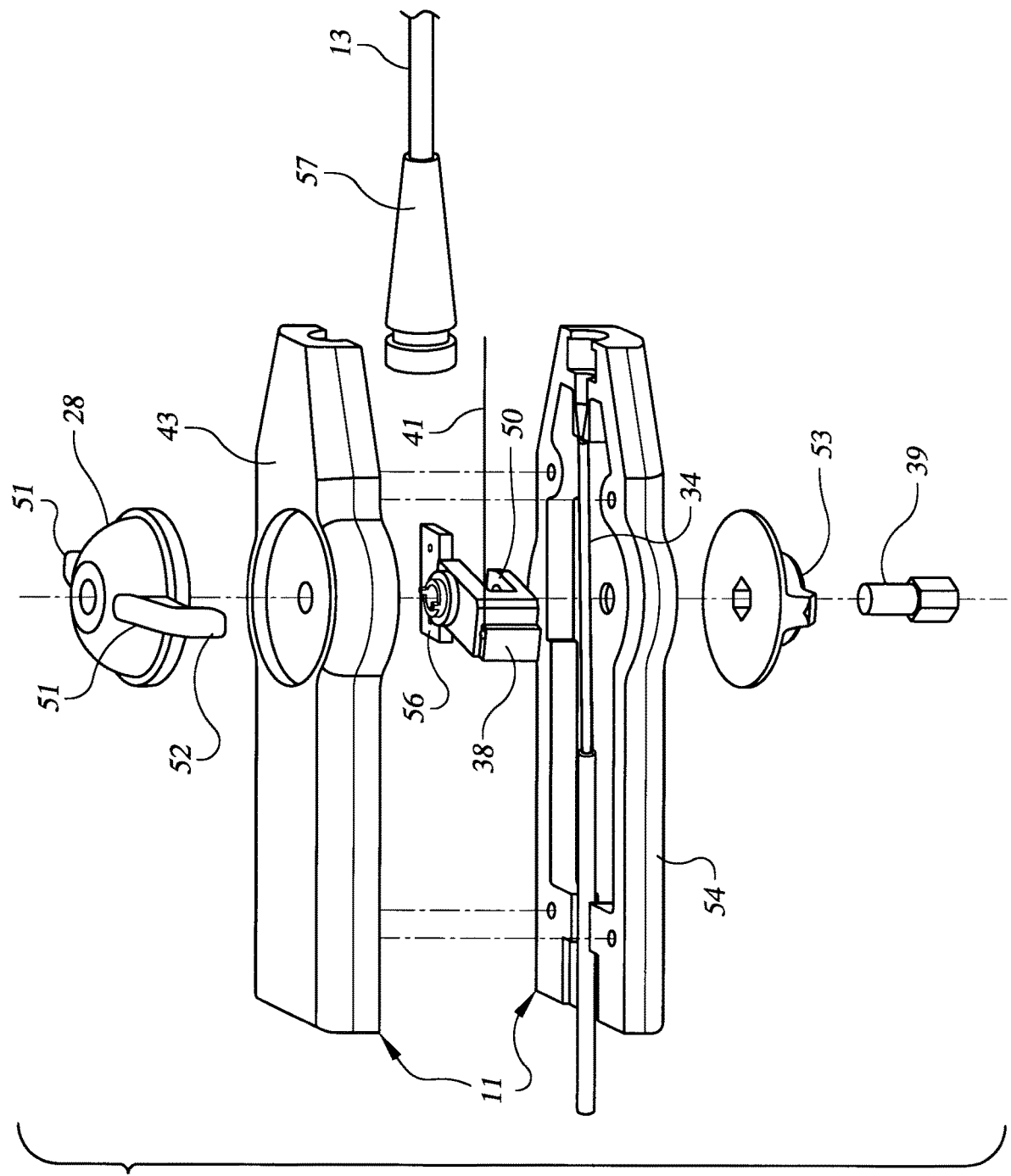
FIG. 4 shows an exploded view of the mechanism components inside the guide catheter handle.

FIG. 4 shows an exploded view of another steering guide catheter handle. In this version, the steering knob 28 is centered on the centerline of the handle. The crank 38 therefor rotates about the center of the catheter handle. The first extension tube 34 is also located on the centerline, and passes through center aperture 50 of the crank. As in FIG. 3, the steering knob 28 for the pullwire 41 is attached to the crank 38 through one of the housing halves, in this case the upper half 43. The steering knob causes the crank 38 to rotate about the pin which tensions the pullwire 41 when the steering knob 28 is actuated. As shown in FIG. 4, the steering knob is fitted with control levers 51 extending radially beyond the width of the handle with bosses or arms 52 extending downwardly along the side surface of the handles. The rotational travel of the steering knob 28 is thereby limited in both directions by the interference of the bosses and the housing. This prevents the pullwire 41 from being over tightened or over loosened by the operator, and prevents crimping of the first extension tube 34 by the crank.

A friction knob 53 is attached to the outside side of the bottom handle half 54, and is secured to the crank with the pin 39 which is inserted through the bottom handle half 54. The user turns the friction knob 53 that is coupled to a flat friction plate 56 and the crank via the pin 39 inside of the handle 11 to increase or decrease the tension on the steering knob.

Figure 5:
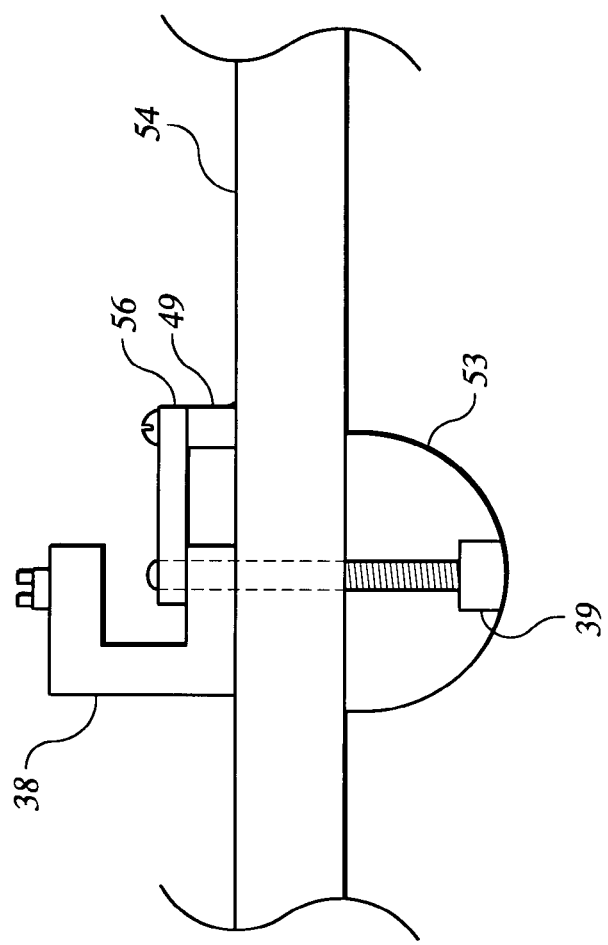
FIG. 5 shows a close-up view from the side of the construction of the tensioning mechanism.

FIG. 5 shows the interaction between the crank 38, the friction plate 56, the pin 39, and the friction knob 53. The friction plate is mounted to the housing via the bosses 49, and is coupled with the crank by the pin. As the friction knob is turned, the pin is turned which tightens the fiction plate down onto the crank. The level of friction can be adjusted from loose to locked, depending on the user's preference.

Referring again to FIG. 3, the pullwire 41 extends from the steering crank 38 up into the guide catheter tube 13 of the steerable guide catheter 6, entering the guide catheter tube 13 just proximal to the conical strain relief 57 in the distal portion of the handle halves. Where the guide catheter tube comprises a distinct outer tube and a liner (that is, where the guide catheter tube comprises a braided tube with a fluoropolymer liner, and the first extension tube 34 is a continuation of the liner beyond the proximal end of the braided tube), the pullwire may be routed between the two. Where the guide catheter tube is constructed in a single piece, the pullwire may be routed into a side lumen in the wall of the guide catheter tube.

Figure 6:
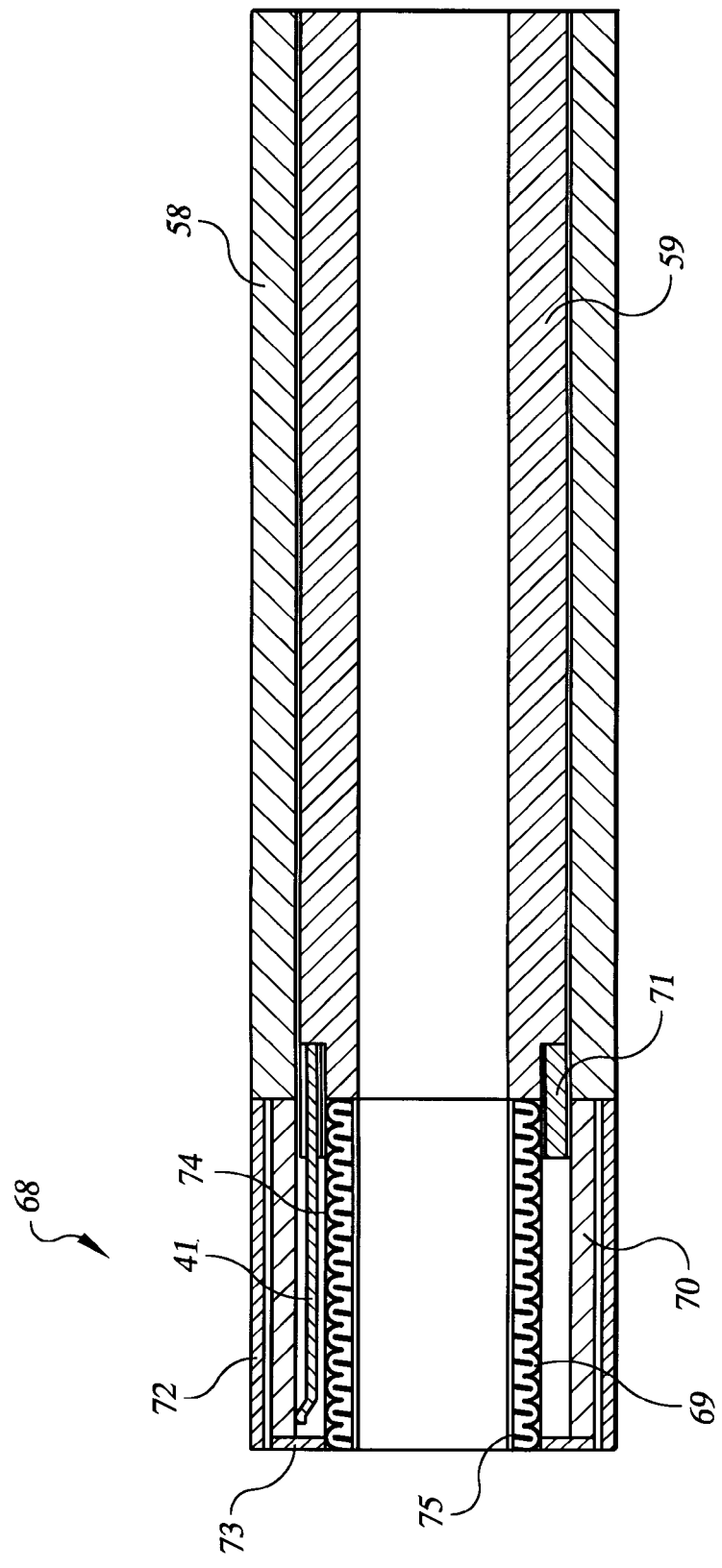
FIG. 6 shows a cross-section view of the construction of the guide catheter tubing assembly.

Preferably, the guide catheter tube 13 is comprised of an outer shaft and an inner tube, as shown in FIG. 6. The outer catheter shaft 58 is typically Pebax that is between 72 D and 25 D in durometer or hardness. It is reinforced with stainless steel wire braiding that is composed of 45 picks per inch of 0.0025" diameter round wire braided in an overlapping pattern for strength, flexibility and torque transmission. The outer catheter shaft 58 is typically 0.118" in outer diameter, 0.091" in inner diameter and 40 to 150 centimeters in length. The inner tube or liner 59 (which makes up the first extension tube 34) is typically polytetrafluoroethylene with an outer diameter of 0.091" and inner diameter of 0.072". Its outer diameter is sized to slip fit within the inner diameter of the outer catheter shaft 58. It may be etched by chemical etchant to improve the adhesion between it and the outer shaft. Alternately it may be plasma treated, flame treated, or roughened to improve the adhesion between it and the outer catheter shaft. A groove for receiving the pullwire may be cut in the outer wall of the inner tube or in the inner wall of the outer catheter shaft. The two shafts may then be melted, bonded, pull-truded, glued or welded to make a unitary tube with a central lumen and an eccentric pullwire lumen.

To lock the guide catheter to the housing of the handle, the outer catheter shaft 58 may be joined to a mounting block 60. The mounting block may be any shape, and the receiving cavities 61 are keyed to the shape of the mounting blocks. When the handle halves are joined together, the mounting block is trapped in the cavities, and rotation in prevented. Preferably, the mounting block has a rectangular prism shape and the cavities in the housing halves are keyed to this shape. The constraint of the mounting block 60 by the handle cavities prevents rotation or translation of the outer catheter shaft 58 relative to the handles.

FIG. 6 is a cross section of the distal segment 29 of the guide catheter tube 13. At the distal end of the device, the guide catheter inner tube 59 is joined to a distal assembly 68. The distal assembly consists of a covered coil 69, deflection tube 70, slotted bushing 71, deflection tube cover 72, and soft tip 73. The covered coil consists of a stainless steel round wire compression spring, typically 0.085" outside diameter by 0.075" inside diameter and 1.5" in length with a coil spacing of 0.015" and a round wire diameter of 0.005". The coil 69 is covered on the outside by a length of 35 D Pebax tubing 74 that has been heat fused through the windings of the coil 69 until it adheres to the fluoropolymer liner 75 that is inside the coil 69. The fluoropolymer liner 75 is typically polytetrafluoroethylene that is between 0.0005" and 0.002" thick, etched on the outside by chemical etchant and slip fit to the inside of the compression spring coil 69. The heat fusing of the Pebax tube 74 through the coil 69 to the fluoropolymer liner 75 makes this distal assembly a unitary composite.

The covered coil assembly sits inside of a slotted cylinder or bushing 71 that spans the joint between the proximal grooved PTFE liner 59 and the distal section of the catheter. The slotted bushing is a stainless steel tube that has had a slot machined or ground into it to allow the pullwire 41 to move freely. The slotted bushing 71 is glued, welded, or bonded onto both the distal and proximal sections of the catheter, reinforcing this joint. The slotted bushing is typically 0.095 OD, 085 ID, and 0.500" in length with a 0.020" wide slot entirely through its length.

Figure 7:
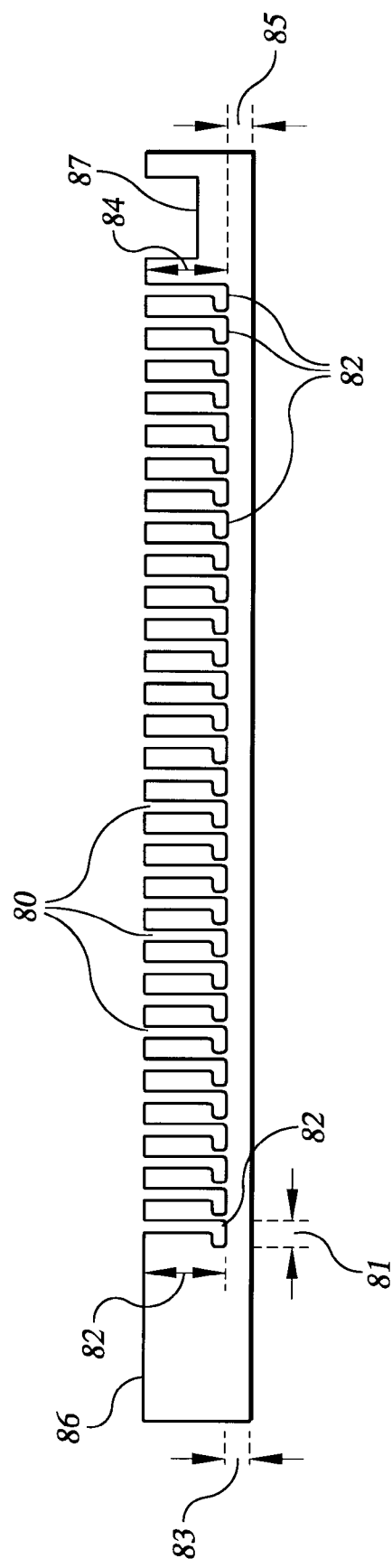
FIG. 7 shows a side view of the deflection tube from the guide catheter tubing assembly.

Assembled over the bushing 71 on the distal portion of the catheter is the slotted deflection tube assembly. The deflection tube 70 consists of a round stainless steel or nitinol tube with a specific pattern of slots machined into it as shown in FIG. 7. The pattern of slots controls the shape that the distal portion of the catheter bends in and the sequence in which its sections bend. The preferred deflection tube is 0.110" OD, 0.100" ID, by 1.570" long. It has a pattern of thirty (30) hook-shaped slots 80 machined, ground, cut, lasered or EDM'ed into it. The slots 80 are spaced at a distance of 0.040" from one another. Each slot is 0.014" wide (referring to the longitudinal width, measured along the long axis of the tube). The length 81 of the hook is 0.032" long. The slots 80 are cut to varying depths in the deflection tube 70 to control the shape of the tube's bending. The most proximal slots are cut to a depth 82 of 0.090", leaving a spine thickness 83 of 0.010". The slots get progressively deeper from proximal to distal end, in groups of five (5). The final five (5) slots in the deflection tube 70 are cut to a depth 84 of 0.094", leaving a spine depth 85 of 0.006" in the deflection tube. The proximal unslotted portion of the deflection tube (marked as item 86) joined to the slotted bushing 71, as shown in FIG. 6.

Referring back to FIG. 6, the distal end of the pullwire 41 is attached to the deflection tube 70 near the distal end of the device. The pullwire 41 is preferentially welded to the inside of the deflection tube 70. The pullwire 41 can also be glued, brazed or mechanically fixed to the inside of the deflection tube 70. The pullwire 41 can alternately be affixed to a C-shaped section of nitinol or stainless steel tubing of the same or similar dimensions as the deflection tube itself. The C-shaped portion can be welded, soldered, brazed, glued or otherwise joined to the deflection tube, creating a unitary structure and an anchor for the pullwire 41. The preferred design consists of a pullwire 41 attached to a C-shaped portion of stainless steel tubing of the same diameter and thickness as the deflection tube 70. The C-shaped pullwire assembly is fit into a cavity 87 (FIG. 6) of the same size that has been machined out of the deflection tube 70.

The delivery catheter shown in FIG. 8 is designed to work with the steerable guide catheter described in FIGS. 2 through 7. The delivery catheter consists of a handle 14 attached to a drug delivery catheter tube 16. The handle 14 has one or more Luer fittings, including one Luer fitting 31 on side arm 90 and a centrally located Luer fitting 32 on the proximal terminus of the central lumen. The centrally located Luer fitting on the proximal terminus is in fluid communication with a central or first lumen 88 of the drug delivery catheter, and thus in fluid communication with the hollow helical tip 9 and thus provides a pathway for the infusion of therapeutic agents. The side arm 90 connects to a side lumen or second lumen 89 in the drug delivery catheter, which in turn connects to an opening (not visible in this view) at the base of the helical tip 9 and is intended for the infusion of radiopaque contrast medium or other therapeutic agents. The preferred embodiment has non-symmetrical arms, or Luer attachment points. These accentuate the difference between the functions of the two Luer fittings. The handle can also be marked with words or icons or colors to distinguish between the two lumens and their purposes.

The handle 14 is typically constructed of machined, cast or molded engineering thermoplastic such as polycarbonate, urethane, ABS or the like. The handle is generally rounded so that the surgeon can easily rotate it. The outside diameter of the handle is typically 0.500 inches and is kept small to keep the weight and bulk of the device to a minimum. The handle has a flattened portion 91 machined or molded into it. The flattened portion 91 serves to increase the surgeon's grip on the device and allows the surgeon to count revolutions of the handle by touch rather than by sight when the device is in use.

The handle 14 is joined to one or more concentric docking segments 92 and 93 at the handle's distal end. The docking segments are typically thin-walled stainless steel, aluminum, PEEK, Pebax, urethane, or liquid crystal polymer tubes. Their outside diameter is sized to fit into the corresponding hole in the steerable catheter handle 11 and their mating tubes (the first extension tube 34 receives the distal docking segment 93 while the second extension tube 35 receives the proximal docking segment 92) in the steerable guide catheter while their inside diameters are large enough to allow the braided delivery catheter tube 16 to pass within them. The distal faces of the docking segments 92 and 93 may be radiused or chamfered to ease their insertion into mating parts. The docking segments 92 and 93 are typically 0.118"

in outside diameter, 0.065" inside diameter and 4.6" in length. The total length of the docking section is chosen to begin the docking process with the handle of the steerable guide catheter before or at the same time that the end of the delivery catheter will be exiting the outer guide. The length of the docking portion limits the amount of delivery catheter that can be extended from the distal end of the guide catheter when in use, in concert with the lengths of the outer guide and delivery catheter shafts. The docking segments also provide a transition in stiffness between the rigid handle and the flexible catheter shaft.

The proximal docking segment 92 is the more rigid section, and facilitates insertion of the drug delivery catheter into the outer guide or hemostatic "Y" adapter during use. The distal docking segment 93 is the more flexible portion of the strain relief, and serves to prevent kinking of the catheter shaft during handling by the physician, and also resists the crushing or clamping of the hemostatic-Y seal on the delivery catheter during use. This keeps the infusion lumens open while preventing blood loss from the devices during use. The smooth outer diameter of the strain relief allows easy sliding of the delivery catheter within the outer guide or hemostatic-Y and easy rotation in either the clockwise or counterclockwise directions while blood loss is prevented by the hemostatic-Y.

FIG. 9 shows a cross section of the handle of FIG. 8 through the top view of the delivery catheter. Inside the handle 14, there is a dual lumen tube 94. This dual lumen extrusion 94 has an outer diameter of 0.035" and a wall thickness of 0.003". The lumens of the tube are preferably of different sizes, since some fluids are to injected in large doses while others are to be injected in very small doses. The larger of the two lumens has an area of $3.74 \times 10^{-4}$ in$^2$ and carries the more viscous of the two solutions used by the physician, typically radiopaque contrast medium or a mixture of contrast medium and saline. This lumen is connected to the tip of the 15-gauge needle Luer 31 mounted in the side arm. The smaller lumen, which has an area of $2.02 \times 10^{-4}$ in$^2$, is connected to the 27-gauge needle Luer 32 by a stainless steel hypo tube 95 and tube 96. The hypo tube 95 is typically 0.016" OD and 0.008"ID. The hypo tube is inserted into the smaller lumen of the double-"d" tubing 94. It inserts into a round Pebax tube 96 with an outer diameter of 0.030" and an inner diameter of 0.018".

The outer shaft 97 of the delivery catheter tube 16 fits over the dual lumen tubing 94 and within the docking segments 92 and 93 and handle 14. It is typically a round, multi-durometer, stainless steel braid reinforced Pebax shaft with an outer diameter of 0.062" and an inner diameter of 0.044". The Pebax durometer typically changes from 75 D on the proximal end for good pushability to 63 D or 55 D or 35 D on the distal end for good bendability, steerability or tracking, as the case may be. The stainless steel braid reinforcement enhances the ability of the shaft to transmit torque from the handle to the distal end of the device and to elastically bend around curves without kinking or collapsing.

The outer shaft 97 of the drug delivery catheter tube 16 is joined to a flexible coil about 4" proximal to the distal end of the device. The shaft and coil are joined by gluing, bonding, welding, soldering, or crimping them both to a joining sleeve or bushing. The joining sleeve or bushing is typically a thin-walled stainless steel tube. Its typical dimensions are 0.042" outside diameter by 0.038" inside diameter by 0.400" in length. It may alternately be constructed of a thermoplastic, thermoset or elastomeric polymer. Its length is minimized to limit the stiffness of the joint while maintaining adequate bending, torsional, compression, and tensile strength to the joint between the braided Pebax tube and the distal coil shown in FIG. 8.

Referring again to FIG. 8, and torque-transmitting coil 98 is constructed of a 5 filar winding of round stainless steel wire, wound in a right hand direction. The outer diameter of the coil is typically 0.059", the inside diameter is 0.043" and the length is typically 4.1" long. The coil 98 is very flexible in bending but stiff in torsion in either direction. The flexible design of the coil 98 allows it to elastically bend around very tight radius curves and still transmit torque, tension and compression. The coil may be alternately constructed with flat stainless steel wire, or nitinol wire, or with a different filar count, or bi- or tri-directional for greater torque transmission in both directions. The end of the coil 98 is trimmed and flattened to keep it smooth and atraumatic. The end of the coil can be glued, welded, soldered or brazed to itself to prevent wires from unraveling. Alternately it can have a polymer or elastomeric soft tip bonded to its distal end (not shown). It can be constructed of platinum or platinum/iridium alloy for increased radiopacity or have radiopaque markers affixed to it or within it.

The coil 98 terminates at the distal end of the device coincidentally with the end of the dual lumen tubing 94. The end of the double-d tubing 94 can be bonded into the end of the coil 98 for reliability. The larger lumen of the double-d tubing 94 is left open at this distal end for infusion of fluid from the side arm 31 on the proximal handle. The smaller lumen is connected to the hollow helical tip 9 so that central needle hub is in fluid communication with the lumen of the hollow helical tip.

The hollow helical tip 9 consists of stainless steel hollow tubing wound into a specific shape and sharpened. The size of the helical tip 9 is chosen to allow an adequate rate of infusion of therapeutic liquid through it and reliable anchoring in tissue, especially cardiac tissue. The proximal end of the helical tip 9 is straightened and glued or bonded into the smaller lumen of the double-d tubing 94, typically with cyanoacrylate, epoxy, or urethane adhesive. The tubing used to construct the helical tip 9 is typically 0.016" OD and 0.008" ID stainless steel hypodermic tubing. The helical tip 9 is wound into a right-handed (clockwise) spiral with an outer pitch diameter of 0.048". The spacing between the turns of the helical tip 9 is typically 0.051". The helical tip 9 typically consists of three or more full turns, and is generally 0.350" in usable length. The distal open end of the helical tip 9 is sharpened into a point to ease insertion into tissue.

Figure 10:
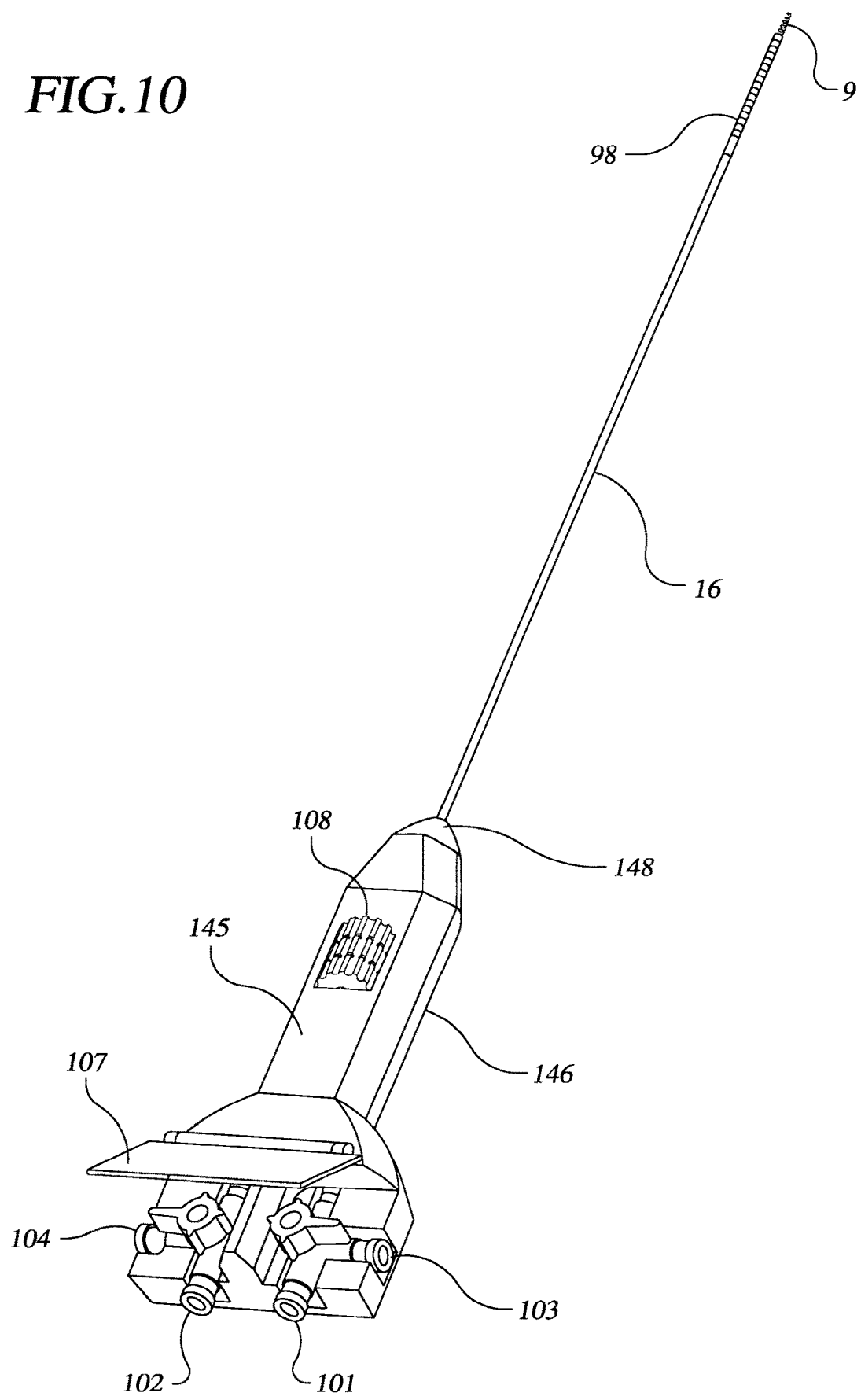
FIG. 10 is an isometric view of the delivery catheter shown in FIGS. 1 and 2.
Figure 11:
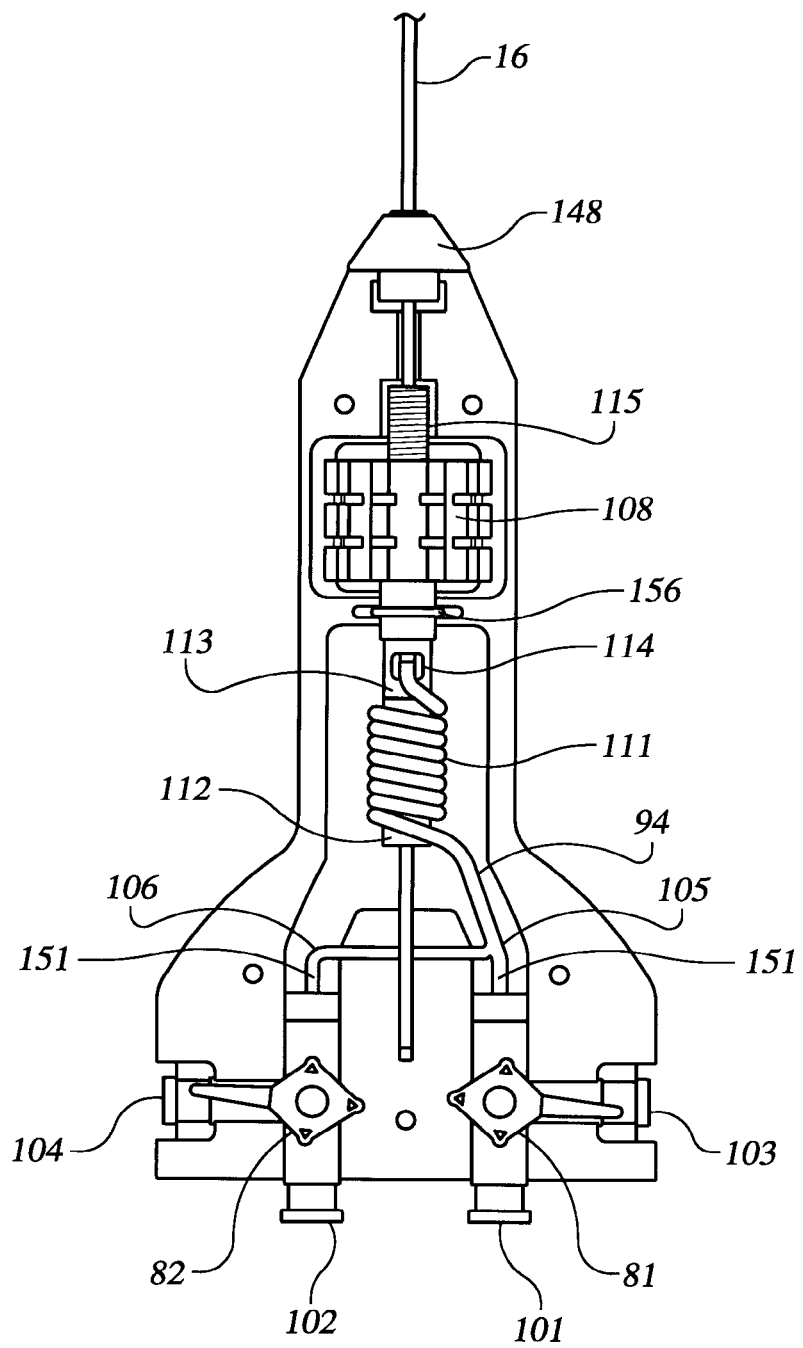
FIG. 11 is a top-cover-removed view of the delivery catheter handle of FIG. 10, showing the internal components.

FIG. 10 shows the design of another delivery catheter that works with the outer guide. The same device is shown in FIG. 11 with the top handle half removed to reveal the internal components. The most proximal part of the handle contains two three-way stopcocks 101 and 102 with side arms 103 and 104, respectively. The stopcocks 101 and 102 allow the user to control fluid delivery sources such as syringes or infusion tubes and route fluid from any one of the ports to one or the other remaining ports. In this delivery catheter, one stopcock is connected to the contrast infusion lumen (the larger lumen) through connecting tube 105, while the other stopcock is connected to the therapeutic infusion lumen through connecting tube 106. The side arms 103 and 104 of the stopcocks are used to flush out excess air from the system, excess infusion liquid from the system, or to draw in more fluid for infusion from an external fluid reservoir. The stopcocks are also covered by a cover 107 that rotates about a hinge on the upper housing. This rotating cover 107 allows the surgeon to access the stopcocks 101 and 102 to operate the stopcocks and to attach fluid infusion devices to them when the cover is rotated up, but covers the stopcocks when access is not needed. Covering the stopcocks 101 and 102 prevents accidental changes to the fluid routing and helps keep the area clean and visible during use. The cover 107 also provides the surgeon with a comfortable and secure area to grip the delivery catheter handle while manipulating the devices. The cover may be manufactured from an opaque, clear, or translucent polymer or plastic. Inset in the middle of the handle is the thumbscrew 108, which is used by the surgeon to turn and advance the helical tip 9 of the device into tissue. The distal tip of the catheter is physically connected to the thumbscrew via the drug delivery tube 16, which is connected to the torque transmitting coil 98 in the same manner as the previous delivery catheter described in FIG. 8.

As shown in FIG. 11, the distal openings of the stopcocks are connected to tubes 105 and 106. One stopcock connects to the larger lumen of the internal Pebax double-d tubing 94. This is usually the radiopaque contrast lumen. The other stopcock connects to the smaller of the double-d tube lumens. This is the therapeutic fluid lumen. The proximal segment of the double-d tubing 94 is wound into a helix 111 and held in place (and in shape) by a mandrel 112 mounted inside the handle. The mandrel is typically 0.125" outside diameter. The mandrel is slidably and rotatably fitted to receiver 113 to allow easy assembly of the coiled double-d tubing 94. The receiver includes a side aperture 114 which provides a pathway for the tubing into a central lumen in the thumbscrews and continuation into the drug delivery tube.

The coiling of the dual lumen tubing allows the tubing to take up variations in length when the device is being used. The double-d tube is typically coiled into a helical shape with an outside diameter of 0.250" and a coil length of 1 inch. The coiling is accomplished by winding and heat-treating on a mandrel during manufacturing. The thumbscrew is the control used by the surgeon to rotate the catheter tube 16 and distal helical tip 9. One of the cylindrical ends of the thumbscrew 108 has an external thread 115 that mates with an internal thread in the housing. Rotation of the thumbscrew 108 in a clockwise direction causes the thumbscrew 108 to move forward (which drives the catheter tube 16 forward while it rotates). Rotation in the counterclockwise direction causes the catheter tube 16 to move backward. The thumbscrew 108 is accessible to the surgeon through windows on both the top and bottom housings of the handle. The length of the threads 115, size of the thumbscrew body, and size of the windows in the upper and lower housings control the amount of forward and backward travel of the catheter tube 16 relative to the handle. This interaction controls the number of turns that the distal helical tip 9 can be screwed into tissue. The pitch of the threads in the housing and on the thumbscrew controls the rate at which the catheter is driven forward or backward and may be matched to the pitch of the distal helical tip 9 for a 1 to 1 relationship between thumbscrew and helical tip 9.

The drug delivery catheter is inserted into the pre-installed steerable or fixed guide through the hemostatic "Y" adapter on the back of the guide. Infusion syringes or lines may be attached to the Luer fittings at the proximal end of the handle at any time. Translation of the delivery catheter handle relative to the guide handle causes the tip of the delivery catheter to advance closer to the tip of the guide. When the rigid strain relief of the delivery catheter enters the hemostatic "Y", the handles of the two devices become docked or locked in bending. They may still be translated and rotated relative to one another, but they are rigid in bending in all degrees of freedom.

The guide distal tip is steered into place, the delivery catheter is extended from the distal tip of the guide by translating the handles relative to one another, and the helical tip is anchored in tissue by turning of the thumbscrew in the clockwise direction. In this embodiment, the handle of the delivery catheter is not rotated to anchor the helical tip in the tissue; only the thumbscrew is rotated. Inside the handle, the coiled double-d tubing expands and contracts to take up this motion between the rotating and advancing helical tip and the stationary infusion stopcocks. After anchoring in tissue, the surgeon may deliver radiopaque contrast medium to confirm location from the lumen that ends at the base of the helical tip, or through the side arm of the hemostatic "Y" and through the guide around the delivery catheter, or infuse therapeutic agent into the anchored tissue through the sharpened helical tip. When delivery is complete, the physician removes the helical tip from the tissue and moves it to another location or removes the system from the body.

Figure 12:
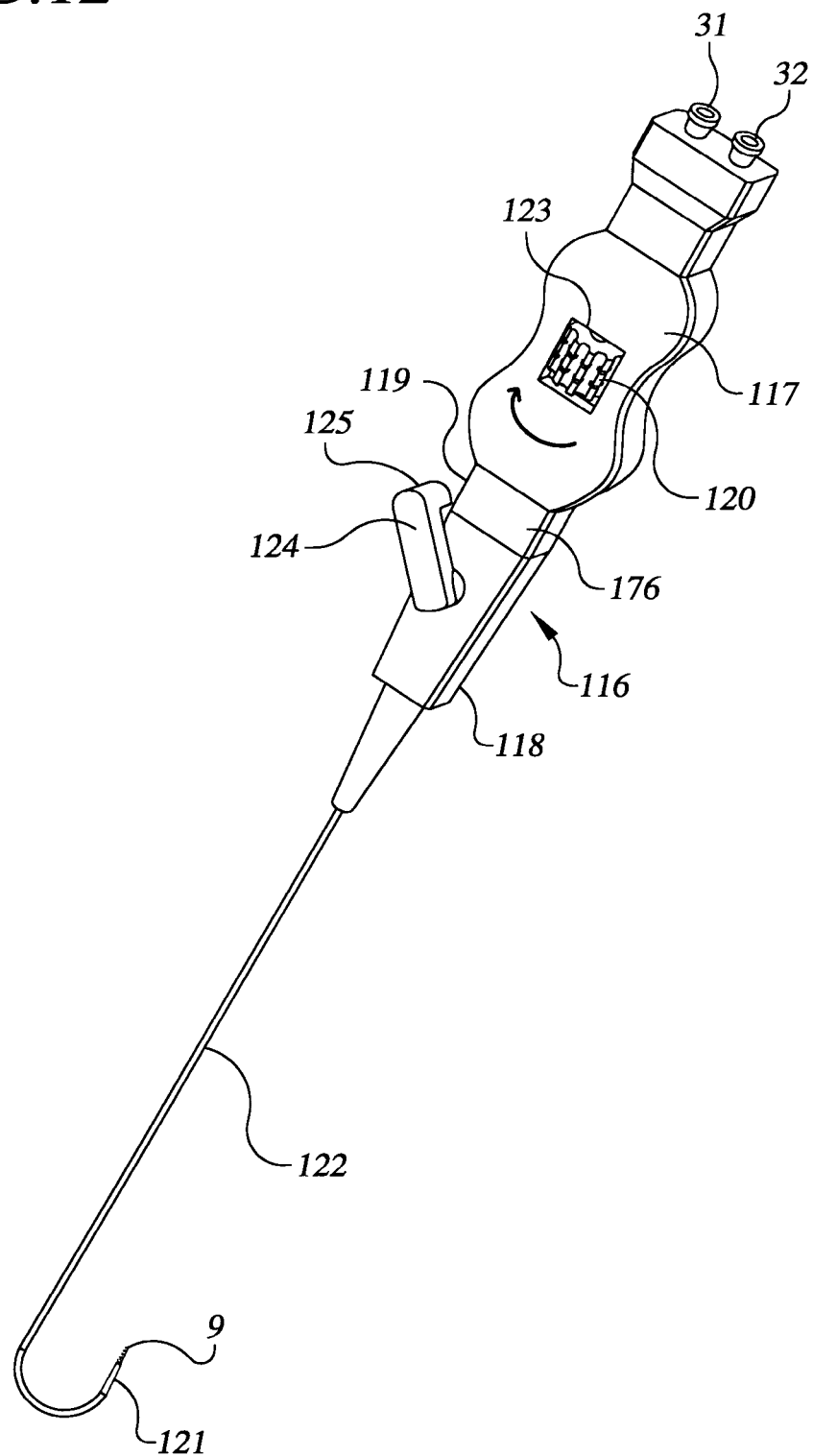
FIG. 12 is an isometric view of an alternate embodiment of an integrated steerable guide and delivery catheter device.

FIG. 12 shows an integrated cardiac drug delivery catheter system. It is a unitary device that incorporates separate mechanisms for steering the distal segment of the catheter and for delivering therapeutic agents to the target tissue through the helical tip on the distal tip of the catheter. The mid-portion of the handle 116 consists of a sliding grip 117 that is mounted on and translates relative to the main body 118 of the handle. The sliding grip 117 can translate relative to the handle 116, along the sliding portion 119, but it cannot rotate. The length of travel of the sliding grip 117 is set by stops in the main body 118 of the handle. Mounted in the sliding grip 117 is thumbscrew 120. This thumbscrew 120 is held on journals inside the housing and has one end that threadably engages matching threads inside the sliding grip 117, similar to the configuration of FIG. 10.

This thumbscrew 120 is permanently attached to the drug delivery tube 121 (which is similar to the drug delivery catheter tube 16 of the earlier Figures, but in this embodiment is integrally attached to the guide catheter). Moving the sliding grip 117 forward translates the drug delivery tube 121 and thumbscrew 120 forward relative to the steerable outer tube 122. The thumbscrew 120 is accessible from either side of the handle, and the cutout 123 is provided on both sides of the sliding grip 117. When the thumbscrew 120 is rotated in the clockwise direction (when viewing the handle from the back), the threads drive the thumbscrew 120 forward relative to the sliding grip 117. The thumbscrew then rotates and translates the drug delivery tube 121 and the helical tip 9 on the end of the device. The rotation may continue until the thumbscrew 120 hits a stop on the sliding grip 117 or until the surgeon decides enough rotation has occurred. The thumbscrew is threaded and engaged with internal threads of the sliding grip, in the same fashion shown in FIGS. 10 and 11. The threading of the thumbscrew 120 and the sliding grip 117 can be equal in pitch to the helical tip if desired, or can differ if more or less mechanical advantage is desired.

Distal to the sliding grip 117 on the handle is the steering knob 124. The steering knob 124 pivots about an axis in the handle. Inside the handle is a pass through rotating element such as those shown in FIG. 3 or 4. Rotation of the steering knob 124 pulls on the steering pullwire, which causes the distal end of the steering tube to curve. The steering knob 124 has a downwardly extending boss 125 that wraps around the side of the housing so that it can be accessed from either side of the device by the surgeon. The boss also prevents the user from curving the device too tightly and prevents the pullwire from becoming too loose in its other stopped position.

The integrated system works in a similar manner to the independent systems previously described. The doctor inserts the device into the femoral artery through a hemostatic sheath. The device is routed up the arterial system and over the aortic arch in a retrograde direction. When the tip of the device nears the aortic valve, the steering handle is actuated and the distal tip of the device is curved into a tight 180-degree shape. The curved tip is advanced into the ventricle and the catheter may be straightened. The doctor then steers the tip of the device toward the area to be treated and advances the inner catheter until the helical tip touches the tissue. The thumbscrew is then turned and the helical tip is anchored into the tissue. The doctor may then infuse therapeutic agent through the helical tip or imaging agent through the outer catheter to see the position and structure of the heart. Once the intervention is complete, the doctor can move to another position or remove the device from the body.

Figure 13:
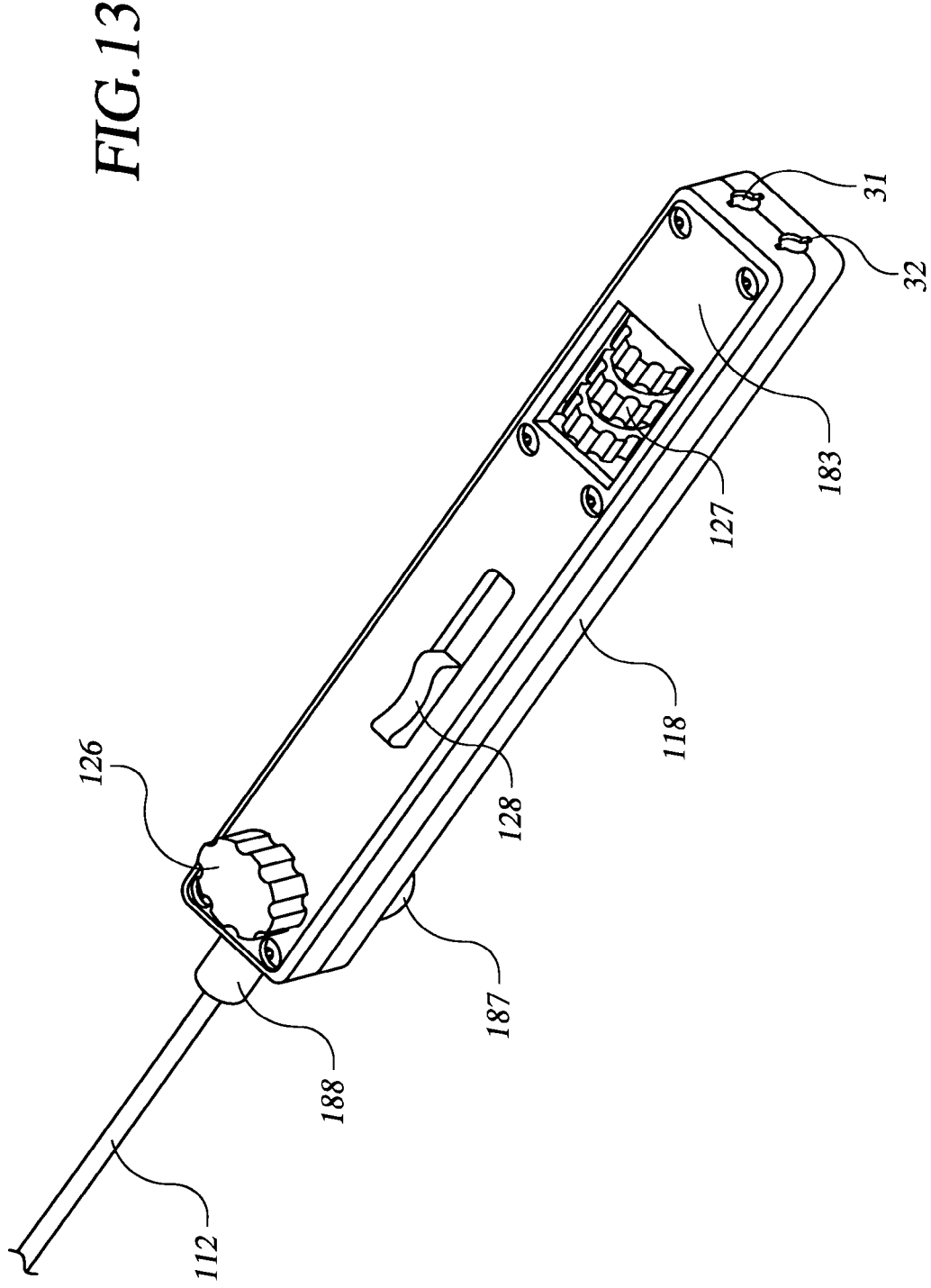
FIG. 13 is an isometric view of the handle of an alternate embodiment of an integrated steerable guide and delivery catheter.

An alternate embodiment for an integrated system is shown in FIG. 13. This system has the features of both the steerable guide and delivery catheter built into one device. As in the embodiment of FIG. 12, a steering knob 126 controls the steerable guide tube, thumbscrews 127 rotate the drug delivery tube within the steerable guide tube. A thumb slide 128, located distal to the thumbscrew, is fixed inside the handle to the drug deliver tube. The thumb slide may be translated longitudinally to move the drug delivery tube distally and proximally within the steerable guide tube, while the thumbscrew remains stationary relative to the handle.

Figure 14:
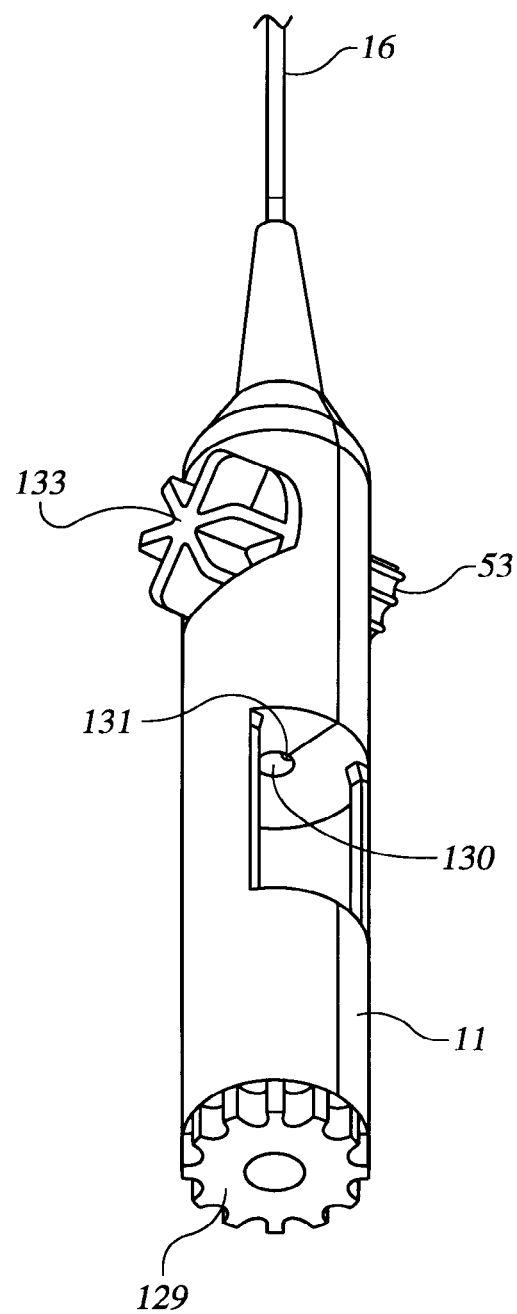
FIG. 14 is an isometric view of the handle of another alternate steerable guide embodiment. The steerable guide is dockable with its delivery catheter.
Figure 15:
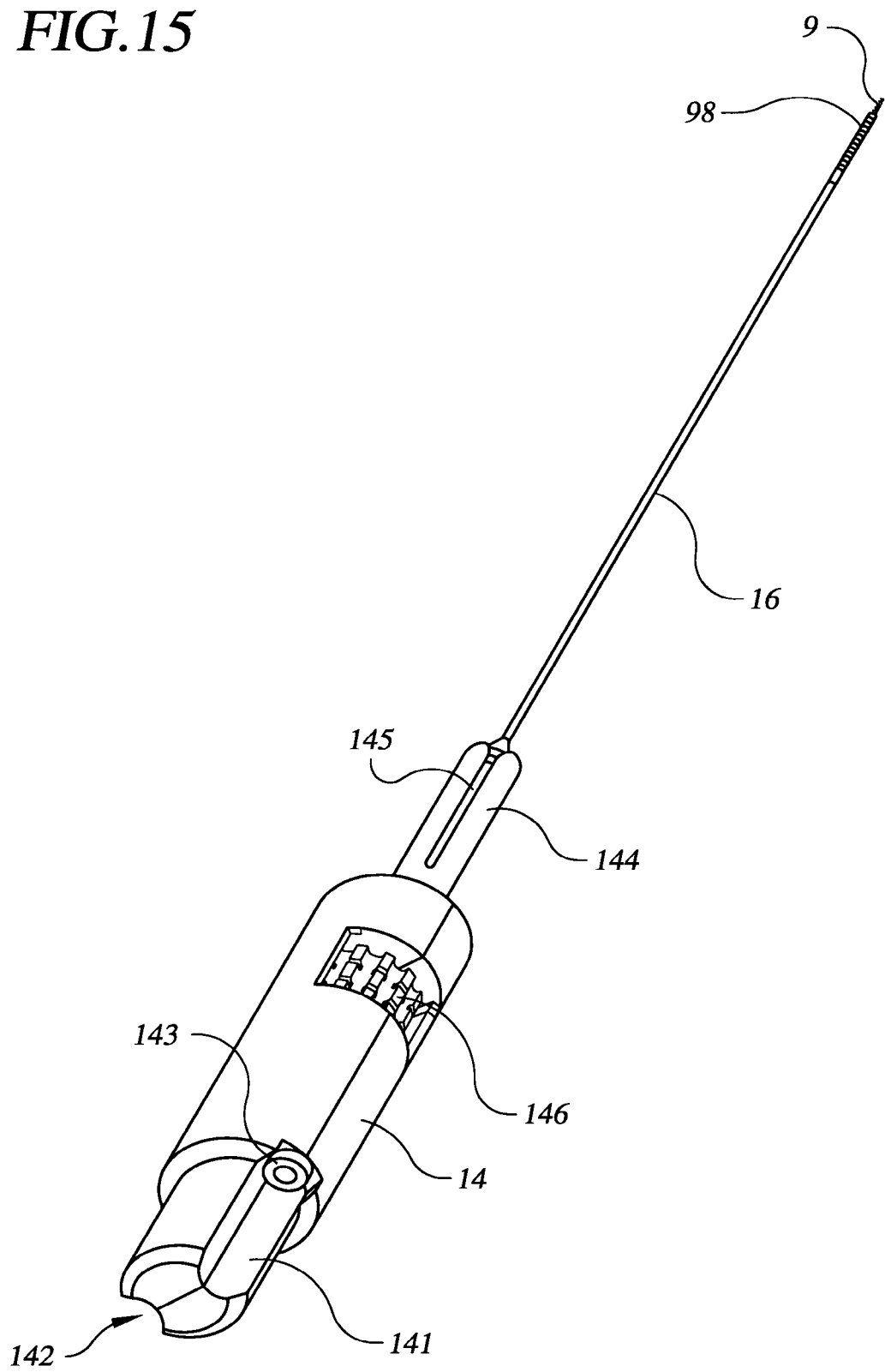
FIG. 15 is an isometric view of an alternate delivery catheter that docks with the steerable guide in FIG. 14.

FIGS. 14 and 15 show another embodiment of the steerable guide and delivery catheter. FIG. 14 shows a steerable guide catheter which can accommodate the drug delivery catheter of FIG. 15. FIG. 15 shows a delivery catheter that fits within and works with the steerable guide in FIG. 14. In this system, the outer guide can be inserted into the body over a guidewire and then the delivery catheter can be inserted into the steerable guide. Once the nose of the delivery catheter engages in the mating cavity in the steerable guide housing, the devices are docked and fixed in bending. They can still be translated and rotated relative to one another, but not bent. Their use and operation is similar to the previously described dockable catheters.

The steerable guide shown in FIG. 14 has a removable collet-adjusting ring 129 on the proximal end of the handle. This ring is threaded into the back of the steerable guide handle and has internally deflectable fingers or a crushable packing. As is it turned in a clockwise direction, its inner diameter shrinks due to bending of the collect fingers or deformation of the packing. Rotation of this ring will lock a tube passing through the ring to the handle. Inside the housing of the guide handle is a smooth constant diameter bore 130 that is sized to accept the nose of the delivery catheter shown in FIG. 15. This bore may also have a protruding aligning pin, rib, or set screw 131 that can prevent the delivery catheter from rotating within this bore, while still allowing the delivery catheter to translate within the bore. The aperture 132 in the side of the steering catheter handle 11 will permit access to the thumbscrew or other operating mechanism of the drug delivery catheter after it is inserted into the guide catheter handle. A steering knob 133 functions in the same manner as the steering knob in the prior embodiments.

FIG. 15 shows the delivery catheter that is designed to work with the dockable steerable guide catheter shown in FIG. 14. As with the prior embodiments, the drug delivery catheter includes the drug delivery tube 16, the drug delivery catheter handle 14, The handle also has a syringe mounting assembly 140 with circular receiving channels 141 and 142 to partially protect the bodies of the syringes when they are connected to the Luer fitting 143 and a similar Luer fitting on the opposite side of the syringe mounting assembly. The Luer fittings are aligned in parallel to the long axis of the syringe mounting assembly and the receiving channels, so that syringes must be disposed partially within the channels in order to connect to the Luer fittings. These cutouts prevent accidental movement or dislodgment of the syringes while still allowing the doctor to access them and view their graduation scales.

The handle includes a distally extending tube 144 which extends distally over the drug delivery catheter tube. The distally extending tube fits within the bore 130. The distally extending tube 144 may have a groove 145 along its length to accept an alignment pin 131 on the inside of the steerable guide catheter handle. The interaction of the pin and groove can prevent rotation of the two devices relative to each other, facilitating rotating of the thumbscrew 146. The length of the distally extending tube 144 of the delivery catheter interacts with the length of the mating cavity in the steerable guide handle to control and limit the length that the delivery catheter distal tip can extend from the distal tip of the steerable guide tube. The distally extending tube 144 of the delivery catheter fits over the main delivery catheter tube 16 with clearance so the delivery catheter shaft can spin when the doctor turns the thumbscrew.

Thus, several embodiments of catheter systems which facilitate the delivery of drugs and therapeutic agents into the heart and other organs of the body have been describe. While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for delivering a drug to a target site within a patient's body comprising:
    a steerable guide catheter comprising:
        a guide catheter having a distal end, a proximal end and a longitudinal axis; and
        a steering pullwire for deflecting the guide catheter;
        a first handle, disposed at the proximal end of the guide catheter, said first handle having a control means operably connected to the steering pullwire; and
    a drug delivery catheter operably connected to the guide catheter, the delivery catheter comprising:
        a second handle secured to the proximal end of the drug delivery catheter, said second handle disposed proximal to the first handle and having a longitudinal axis, a distal end, and a proximal end;
        a delivery catheter having a lumen, said delivery catheter protruding out of the distal end of the second handle and aligned substantially along the longitudinal axis of the second handle and extensible beyond the distal end of the guide catheter;
        a helical drug delivery needle operably connected to the distal end of the delivery catheter; and
        said second handle being operable to rotate and advance the drug delivery catheter within the guide catheter.

2. The system of claim 1 further comprising:
means for routing fluids to be passed through the drug delivery catheter, the fluid routing means operably and rigidly secured to the drug delivery catheter to rotate and advance with the drug delivery catheter.

3. The system of claim 1 wherein the drug delivery catheter further comprises:
a single lumen delivery catheter protruding out of the distal end of the handle and aligned substantially along the longitudinal axis of the handle and extensible from zero to six centimeters beyond the distal end of the guide catheter.

4. The system of claim 1 wherein the drug delivery catheter further comprises:
a dual lumen delivery catheter having a first and second lumen, said delivery catheter protruding out of the distal end of the second handle and aligned substantially along the longitudinal axis of the second handle and extensible from zero to six centimeters beyond the distal end of the guide tube.

5. The system of claim 1 wherein the drug delivery catheter further comprises:
a torque transmitting member, said torque transmitting member being torsionally stiff and laterally flexible, said torque transmitting member being disposed between the helical drug delivery needle and the distal end of the delivery catheter.

6. The system of claim 5 wherein the torque transmitting member is about 4.1 inches long.

7. The system of claim 5 wherein the torque transmitting member is a stainless steel coil about 4.1 inches long.

8. The system of claim 5 wherein drug delivery catheter comprises an outer shaft disposed over a tube, and said torque transmitting member is joined to the outer shaft.

9. The system of claim 8, wherein the outer shaft is characterized by a proximal end and a distal end, and the outer shaft comprises a polymer with a hardness of 75 D at said proximal end and a hardness of 63 D at said distal end.

10. The system of claim 8, wherein the outer shaft is characterized by a proximal end and a distal end, and the outer shaft comprises a polymer with a hardness of 75 D at said proximal end and a hardness of 55 D at said distal end.

11. The system of claim 8, wherein the outer shaft is characterized by a proximal end and a distal end, and the outer shaft comprises a polymer with a hardness of 75 D at said proximal end and a hardness of 35 D at said distal end.

12. The system of claim 1, wherein the guide catheter has an outer diameter of 0.118" or less.

13. A system for delivering a drug to a target site within a patient's body comprising:
a steerable guide catheter comprising:
a guide catheter having a distal end, a proximal end and a longitudinal axis; and
a steering pullwire for deflecting the guide catheter;
a first handle, disposed at the proximal end of the guide catheter, said first handle having a control means operably connected to the steering pullwire; and
a drug delivery catheter operably connected to the guide catheter, the delivery catheter comprising:
a second handle secured to the proximal end of the drug delivery catheter, said second handle disposed proximal to the first handle and having a longitudinal axis, a distal end, and a proximal end;
a delivery catheter having a lumen, said delivery catheter protruding out of the distal end of the second handle and aligned substantially along the longitudinal axis of the second handle and extensible beyond the distal end of the guide catheter;
a helical drug delivery needle operably connected to the distal end of the delivery catheter; and
a thumbscrew disposed on said second handle, said thumbscrew being operable to rotate the helical drug delivery needle within the steerable guide catheter.

14. The system of claim 13, where the thumbscrew is also operable to advance the helical drug delivery needle within the steerable guide catheter.

15. A system for delivering a drug to a target site within a patient's body comprising:
a steerable guide catheter comprising:
a guide catheter having a distal end, a proximal end and a longitudinal axis; and
a steering pullwire for deflecting the guide catheter, the deflection of the distal end greater than ninety degrees from the longitudinal axis; and
a drug delivery catheter operably connected to the guide catheter, the delivery catheter comprising:
a handle having a longitudinal axis, a distal end, and a proximal end;
a delivery catheter having a lumen, said delivery catheter slidably and rotatably disposed within the guide catheter, such that the drug delivery catheter may be advanced from the proximal end of the steerable guide catheter to the distal end of the steerable guide catheter and extended beyond the distal end of the guide catheter, said delivery catheter protruding out of the distal end of the handle and aligned substantially along the longitudinal axis of the handle;
a helical drug delivery needle operably connected to the distal end of the delivery catheter; and
said handle being operable to rotate and advance the drug delivery catheter within the guide catheter.

16. The system of claim 15 further comprising:
means for routing fluids to be passed through the drug delivery catheter, the fluid routing means operably and rigidly secured to the drug delivery catheter to rotate and advance with the drug delivery catheter.

17. The system of claim 15 wherein the drug delivery catheter further comprises:
a single lumen delivery catheter protruding out of the distal end of the handle and aligned substantially along the longitudinal axis of the handle and extensible from zero to six centimeters beyond the distal end of the guide catheter.

18. The system of claim 15 wherein the drug delivery catheter further comprises:
a dual lumen delivery catheter having a first and second lumen, said delivery catheter protruding out of the distal end of the handle and aligned substantially along the longitudinal axis of the handle and extensible from zero to six centimeters beyond the distal end of the guide tube.

19. The system of claim 15 wherein the drug delivery catheter further comprises:
a torque transmitting member, said torque transmitting member being torsionally stiff and laterally flexible, said torque transmitting member being disposed between the helical drug delivery catheter and the distal end of the delivery catheter.

20. The system of claim 19 wherein the torque transmitting member is about 4.1 inches long.

21. The system of claim 19 wherein the torque transmitting member is a stainless steel coil about 4.1 inches long.

22. The system of claim 19 wherein drug delivery catheter comprises an outer shaft disposed over a tube, and said torque transmitting member is joined to the outer shaft.

23. The system of claim 22, wherein the outer shaft is characterized by a proximal end and a distal end, and the outer shaft comprises a polymer with a hardness of 75 D at said proximal end and a hardness of 63 D at said distal end.

24. The system of claim 22, wherein the outer shaft is characterized by a proximal end and a distal end, and the outer shaft comprises a polymer with a hardness of 75 D at said proximal end and a hardness of 55 D at said distal end.

25. The system of claim 22, wherein the outer shaft is characterized by a proximal end and a distal end, and the outer shaft comprises a polymer with a hardness of 75 D at said proximal end and a hardness of 35 D at said distal end.

26. The system of claim 15, wherein the guide catheter has an outer diameter of 0.118" or less.

27. A system for delivering a drug to a target site within a patient's body comprising:
   a steerable guide catheter comprising:
      a guide catheter having a distal end, a proximal end and a longitudinal axis; and
      a steering pullwire for deflecting the guide catheter, the deflection of the distal end greater than ninety degrees from the longitudinal axis; and
   a drug delivery catheter operably connected to the guide catheter, the delivery catheter comprising:
      a drug delivery catheter slidably and rotatably disposed within the guide catheter, such that the drug delivery catheter may be advanced from the proximal end of steerable guide catheter to the distal end of the steerable guide catheter and extended beyond the distal end of the guide catheter, said drug delivery catheter comprising:
      a helical drug delivery needle operably connected to the distal end of the delivery catheter; and
      said drug delivery catheter having a handle on the proximal end thereof, and a thumbscrew disposed said handle, said thumbscrew being operable to rotate the helical drug delivery needle within the steerable guide catheter.

28. The system of claim 27, where the thumbscrew is also operable to advance the helical drug delivery needle within the steerable guide catheter.

* * * * *